United States Patent [19]
Le Fur et al.

[11] Patent Number: 5,604,245
[45] Date of Patent: Feb. 18, 1997

[54] USE OF 4-AMINO-1-(2-PYRIDYL)PIPERIDINES FOR THE PREPARATION OF A MEDICAMENT FOR THE TREATMENT OF CONDITIONS DERIVING FROM DISORDERS OF THE SEROTONINERGIC SYSTEMS MEDIATED BY 5-HT$_3$ RECEPTORS

[75] Inventors: Gérard Le Fur, Montmorency, France; Alberto Bianchetti, Milan, Italy; Antonina Giudice, Milan, Italy; Tiziano Croci, Milan, Italy; Philippe Soubrie, Saint Mathieu de Treviers, France

[73] Assignee: Elf Sanofi, France

[21] Appl. No.: 858,483

[22] Filed: Mar. 27, 1992

[30] Foreign Application Priority Data

Mar. 27, 1991 [FR] France ................................. 91 03735
Mar. 27, 1991 [FR] France ................................. 91 10890
Oct. 15, 1991 [EP] European Pat. Off. .............. 91402753

[51] Int. Cl.$^6$ ................................................. A61K 31/445
[52] U.S. Cl. ................................................. 514/318
[58] Field of Search ........................... 514/318; 546/193, 546/194

[56] References Cited

U.S. PATENT DOCUMENTS 4,409,228  10/1983  Nisato et al. ........................... 514/318

FOREIGN PATENT DOCUMENTS 0021973  1/1981  European Pat. Off. .

OTHER PUBLICATIONS

*European Journal of Pharmacology;* 237 (1993) 299–309; Bachy et al.; "SR 57227A: A Potent and Selective Agonist at Central and Peripheral 5–HT$_3$ Receptors in vitro and in vivo".

*European Journal of Pharmacology;* 163 (1989) 397–398; Schmidt et al.; "Antidepressant Interactions with 5–Hydroxytryptamine$_3$ Receptor Binding Sites".

R. W. Fuller et al., "Neurochemical effects of CM 57227 and CM 57373, two anorectic agents, on brain serotonin neurons in rats," *Neurochem. Int.,* vol. 16, No. 3 (1990), pp. 309–312.

S. Garattini et al., "Reduction of food intake by manipulation of central serotonin. Current experimental results," Dialog Information Services, Inc., File 155, AN=07215162, citing, *Br. J. Psych. Suppl.,* (Dec. 1989), pp. 41–51.

A. W. Schmidt et al., "Antidepressant interactions with 5–hydroxytryptamine$^3$ receptor binding sites," *Chemical Abstracts,* vol. 111, No. 3, 17629k, citing, *Eur. J. Pharmacol.* (1989) pp. 397–398.

*Primary Examiner*—Kevin E. Weddington
*Attorney, Agent, or Firm*—Bacon & Thomas

[57] ABSTRACT

The present invention concerns the use of 4-amino-1-(2-pyridyl)piperidines of general formula (I')

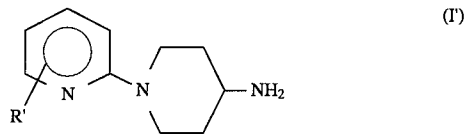

(I')

wherein R' represents hydrogen, a halogen atom, a methyl, methylthio, trifluoromethyl, trifluoromethylthio, (C$_1$–C$_3$)alkoxy, trifluoromethoxy, 2,2,2-trifluoroethoxy, or phenoxy group optionally substituted with a halogen atom, a trifluoromethyl, (C$_1$–C$_3$)alkyl, (C$_1$–C$_3$)alkoxy, (C$_1$–C$_3$)alkylthio, or cyano group, or of a pharmaceutically acceptable salt thereof, for the preparation of a medicament for the treatment or prophylaxis of those conditions deriving from disorders of the serotoninergic systems wherein a serotoninergic action selectively mediated by the 5-HT$_3$ receptors is required, e.g. affective disorders, anxiety, psychotic troubles, constipation.

8 Claims, No Drawings

USE OF 4-AMINO-1-(2-PYRIDYL)PIPERIDINES FOR THE PREPARATION OF A MEDICAMENT FOR THE TREATMENT OF CONDITIONS DERIVING FROM DISORDERS OF THE SEROTONINERGIC SYSTEMS MEDIATED BY 5-HT₃ RECEPTORS

The present invention concerns a new therapeutical use of some 4-amino-1-(2-pyridyl)piperidines.

U.S. Pat. No. 4,409,228 describes the class of 4-amino-1-(2-pyridyl)piperidines of general formula (I)

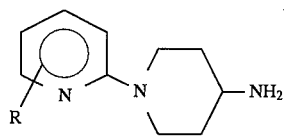
(I)

wherein R may represent hydrogen, a halogen atom, a methyl, trifluoromethyl, ($C_1$-$C_3$)alkoxy, trifluoromethoxy, 2,2,2-trifluoroethoxy, ($C_1$-$C_3$)alkylthio, trifluoromethylthio, or phenoxy or phenylthio group optionally substituted with a halogen atom, a trifluoromethyl, ($C_1$-$C_3$)alkyl, ($C_1$-$C_3$)alkoxy, ($C_1$-$C_3$)alkylthio, or cyano group, and the pharmaceutically acceptable salts thereof, as well as a process for their preparation.

The compounds of formula (I) are there described as anorexigenic agents, essentially devoid of important side effects.

Among the compounds of formula (I), 4-amino-1-(6-chloro-2-pyridyl)piperidine hydrochloride, described in Example 1 of U.S. Pat. No. 4,409,228 and indicated as CM57227 was submitted to those tests necessary for entering clinical trials where it showed to be well tolerated by the patients up to a dose of 10 mg.

It has now been found that the compounds of formula (I) wherein R represents hydrogen, a halogen atom, a methyl, methylthio, trifluoromethyl, trifluoromethylthio, ($C_1$-$C_3$)alkoxy, trifluoromethoxy, 2,2,2-trifluoroethoxy, or phenoxy group optionally substituted with a halogen atom, or a trifluoromethyl, ($C_1$-$C_3$)alkyl, ($C_1$-$C_3$)alkoxy, ($C_1$-$C_3$)alkylthio, or cyano group, as well as their pharmaceutically acceptable salts, described in U.S. Pat. No. 4,409,228 as serotonin uptake inhibitors, are selective 5-HT₃ receptor agonists at peripheral and central level.

More particularly it has been found that the compounds of formula (I) wherein R is as defined above and their pharmaceutically acceptable salts have affinity for 5-HT₃ receptors much higher than that of serotonin or 2-methylserotonin.

It has also been found by means of ex-vivo binding tests, carried out on representative compounds of said class, that the affinity for central 5-HT₃ receptors is markedly higher than that for serotonin uptake sites.

A first object of the present invention is therefore the use of at least one compound of formula (I')

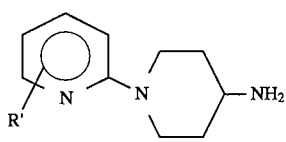
(I')

wherein R' represents hydrogen, a halogen atom, a methyl, methylthio, trifluoromethyl, trifluoromethylthio, ($C_1$-$C_3$)alkoxy, trifluoromethoxy, 2,2,2-trifluoroethoxy, or phenoxy group optionally substituted with a halogen atom, a trifluoromethyl, ($C_1$-$C_3$)alkyl, ($C_1$-$C_3$)alkoxy, ($C_1$-$C_3$)alkylthio, or cyano group, or a pharmaceutically acceptable salt thereof, for the preparation of a medicament for the treatment or prophylaxis of all conditions deriving from disorders of the serotoninergic systems wherein a serotoninergic action selectively mediated by 5-HT₃ receptors is considered to be beneficial.

In the present invention, the term "halogen" identifies one of the four common halogens, fluorine, chlorine and bromine being particularly preferred.

The terms "($C_1$-$C_3$)alkyl", "($C_1$-$C_3$)alkoxy", and "($C_1$-$C_3$)alkylthio" designate groups containing a saturated aliphatic hydrocarbon residue of 1, 2, or 3 carbon atoms, namely methyl, ethyl, propyl and isopropyl.

The pharmaceutically acceptable salts of the compounds of formula (I') comprise the non-toxic salts with mineral or organic acids wherein one or both basic functions of the compounds of formula (I') are salified, such as hydrochlorides, hydrobromides, sulfates, phosphates, succinates, tartrates, fumarates, maleates, pamoates, napsylates, mesylates, tosylates, and the like.

A preferred class of compounds of formula (I') comprises those compounds of formula (I') wherein R' is at position 6- of the 2-pyridyl radical.

An even more preferred class of compounds comprises those compounds of formula (I') wherein R' is hydrogen or a halogen atom or a methyl or ($C_1$-$C_3$)alkoxy group at position 6-.

Another preferred class of compounds comprises those compounds of formula (I') wherein R' represents a halogen atom at position 3-.

4-Amino-1-(6-chloro-2-pyridyl)piperidine and the pharmaceutically acceptable salts thereof, particularly its hydrochloride, 4-amino-1-(6-bromo-2-pyridyl)piperidine and the pharmaceutically acceptable salts thereof, particularly its hydrochloride, 4-amino-1-(6-methyl-2-pyridyl)piperidine and the pharmaceutically acceptable salts thereof, particularly its dihydrochloride, and 4-amino-1-(6-methoxy-2-pyridyl)piperidine and the pharmaceutically acceptable salts thereof, particularly its hydrochloride, are particularly preferred compounds.

The compounds of formula (I') are easily prepared by the method described in U.S. Pat. No. 4,409,228, by reacting the corresponding 2-halopyridine of formula (II)

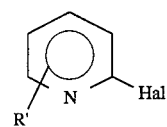
(II)

wherein R' is as defined above and Hal represents a halogen atom, with a blocked 4-aminopiperidine of formula (III)

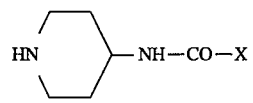
(III)

wherein X represents a hydrogen atom or a ($C_1$-$C_4$)alkyl group, and hydrolysing the thus obtained N-acylated 4-amino-1-(2-pyridyl)piperidine of formula (IV)

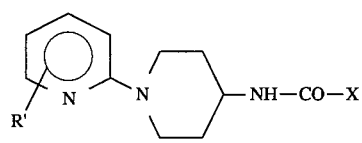
(IV)

under basic or acidic conditions.

A more detailed description of the general process for the preparation of the compounds of formula (I'), as well as some specific working examples, are reported in the above cited U.S. Pat. No. 4,409,228.

The affinity of the compounds of formula (I') for 5-HT$_3$ receptors has been evaluated at first by means of an in vitro binding test using binding sites in the rat cerebral cortical tissue (cfr. G. J. Kilpatrick, B. J. Jones and M. B. Tyers—Identification and distribution of 5-HT$_3$ receptors in rat brain using radioligand binding—Nature, 1987, 330, 746–8) and [$^3$H] BRL 43694 (granisetron), a potent and specific 5-HT$_3$ receptor antagonist as the labeled ligand. The potency of the compounds of formula (I') in displacing [$^3$H] BRL 43694 was compared to that of serotonin and other 5-HT$_3$ receptor agonists (2-methylserotonin and m-chlorophenylbiguanide), as well as to that of the 5-HT$_3$ receptor antagonist ICS 205–930.

For the preparation of cerebral membranes, male rats weighing about 200 g and sacrificed by decapitation were employed. The membrane preparation and the binding test were carried out according to the method described by Nelson and Thomas (D. R. Nelson and D. R. Thomas—[$^3$H] BRL 43694 (Granisetron), a specific ligand for 5-HT$_3$ binding sites in rat brain cortical membranes. Biochem. Pharmacol., 1989, 38, 1963–65). In summary, the cortical tissue from 4 animals was homogenized in 20 volumes of HEPES and kept at 4° C. until used in the binding assays.

The thus prepared membranes contained on the average 7.42±0.11 mg of protein/ml, calculated according to the Lowry method (O. H. Lowry, N. J. Rosenbrough, A. L. Fan and R. J. Randall—Protein measurement with the Folin phenol reagent—J. Biol. Chem., 1951, 193, 265–75) using bovine serum albumin for the determination of the standard curve.

For drug competition studies, 500 μl of membrane suspension was incubated in the presence of 0.5 nM [$^3$H] BRL 43694 (specific activity 61 Ci/mmol) and of different concentrations of cold compounds for 30 minutes at 25° C., in a total volume of 1 ml. The incubation was terminated by filtering rapidly through Whatman GF/B filters which were then rinsed twice with 50 mM HEPES, pH 7.5, (10 ml) at 4 ° C. Aspecific binding was determined in samples containing an excess of ICS 205–930 (1 μM).

Preliminary saturation and kinetic studies were carried out to set up the test. For the saturation studies, 9 triplicate concentrations of [$^3$H] BRL 43694 (0.05–2 nM) were used, determining, for each radioligand concentration, the aspecific binding (in the presence of 1 μM ICS 205–930).

The time course for the association-dissociation of [$^3$H] BRL 43694 to the 5-HT$_3$ sites was followed for 45 minutes, in the absence and in the presence of 1 μM ICS 205–930.

The results were calculated by means of non-linear fitting methods "Accufit saturation" for the saturation studies (H. A. Feldman—Mathematical theory of complex ligand-binding systems at equilibrium: some methods of parameter fitting—Analyt. Biochem., 1972, 48, 317–38) and "Accufit competition" for the displacing studies (H. A. Feldman, D. Rodbord, and D. Levine—Mathematical theory of cross reactive radioimmunoassay and ligand-binding systems at equilibria—Analyt. Biochem., 1972, 45, 530–56).

Scatchard analysis of [$^3$H] BRL 43694 binding revealed a single saturable binding site of high affinity ($K_d$=0.46±0.01 nM; $B_{max}$=7.54±0.07 fmol/mg of protein or 1.12 fmol/mg of wet tissue). The kinetically derived $K_d$=0.5, is in agreement with that obtained by the Scatchard analysis. 0.5 nM [$^3$H] BRL 43694 was therefore employed in the competition studies in order to obtain the affinities of the different test compounds ($K_i$).

In this test, the compounds of formula (I') showed to be much more potent (generally 10 to 20 times more potent) than serotonin and 2-methylserotonin in displacing [$^3$H] BRL 43694.

As an example, the compound of formula (T) wherein R' is a chloro atom at position 6-(CM 57227) showed a $K_i$ of 193 nM, whereas serotonin and 2-methylserotonin $K_i$s are 1195 and 1115 nM respectively.

This affinity for 5-HT$_3$ receptors is also selective. More particularly, the ability of the same compound (CM 57227) to displace a series of labelled specific ligands from different binding sites has been evaluated and the obtained results show that this compound has no affinity ($K_i$>10,000 nM) for 5-HT$_{1A}$ and 5-HT$_{1B}$ receptors, for serotonin uptake sites ([$^3$H] paroxetine displacement test), for adrenergic sites $\alpha_2$, $\alpha_1$ and $\beta_1$ and for dopaminergic sites $D_1$ and $D_2$.

Secondly, it has been confirmed that the compounds of formula (I') wherein R' is as defined above do penetrate the CNS, passing through the blood brain barrier.

To this purpose, ex vivo tests were carried out in mice evaluating the inhibition of [$^3$H] BRL 43694 specific binding to cortical cerebral membranes, 30 minutes after the intraperitoneal (i.p.) administration of increasing doses of representative compounds of formula (I'). In these tests, carried out by following the methodology described by Wood and Piper (J. Psychopharmacol., 1990, 4(4), 290), ID$_{50}$ s (the doses which inhibit by 50% [$^3$H] BRL 43694 binding) at different dilutions were calculated and the ID$_{50}$ at zero dilution was then extrapolated. The compounds of formula (I') submitted to this test showed an ID$_{50}$ (mg/kg i.p.) comparable to that of GR-38032 F, a known selective 5-HT$_3$ receptor antagonist, employed as reference compound.

In particular, CM 57227 showed an ID$_{50}$ i.p., extrapolated to zero dilution, of 1 mg/kg and, by repeating th test but administering the compounds orally, and ID$_{50}$ p.o., extrapolated to zero dilution, of the same magnitude order.

The ID$_{50}$ of CM 57227 for [$^3$H] BRL 43693 is markedly lower than the ID$_{50}$ of the same compound for [$^3$H] paroxetine, paroxetine being a marker of the serotonin uptake sites, evaluated under the same experimental conditions.

CM 57227 was also studied in the "turning" test carried out as described by P. Worms et al. in Life Sciences, 1986, 39, 2199–2208.

Like 2-methyl-serotonin, 4-amino-1-(6-chloro-2-pyridyl)piperidine hydrochloride, injected into the mice striatum, evokes a turning behaviour which is inhibited by 5-HT$_3$ receptor antagonists. Intraperitoneally injected, this compound blocks the antagonism exerted by ondansetron (1 mg/kg i.p.) to the turning behaviour induced by intrastriatal injection of 2-methylserotonin with an ED$_{50}$ of 0.25 mg/kg, dose which is entirely in agreement with the above reported results in the ex vivo tests.

Selective 5-HT$_3$ agonist activity of the compounds of formula (I') was confirmed in vivo in the Bezold-Jarish test. In this test, intravenous administration of the compounds of formula (I') evokes in the anaesthetised rat, a short-lived reduction of heart rate (Bezold-Jarish effect). The intensity of this effect varies depending on the dose and is comparable to that obtained by administering serotonin or 2-methylserotonin.

This effect is inhibited by selective 5-HT$_3$ receptor antagonists (e.g. ICS 205-930 and zacopride), while it is not inhibited by serotonin D receptor antagonists (e.g. methysergide).

More particularly, the Bezold-Jarish effect evoked by the compounds of formula (I') was evaluated using Sprague-Dawley rats weighing from 200 to 300 g, anaesthetised with urethane 1.25 g/kg i.p. The blood pressure was recorded from the carotid artery and heart rate was evaluated, as pulse frequency, by means of a cardiotachometer. A catheter was inserted into the jugular vein for the administration of the substances.

Different doses of the compounds to be tested were administered intravenously in a volume of 0.5 ml/kg and for each compound the $ID_{50}$, i.e. the dose which inhibits by 50% the heart rate in the treated animals, was calculated.

In this test the compounds of formula (I') wherein R' is as defined above showed an $ID_{50}$ lower or comparable to that of 2-methylserotonin.

As an example, the $ID_{50}$ i.v. of CM 57227 is 8.29 μg/kg while the $ID_{50}$ of serotonin and 2-methyl-serotonin is 13.61 and 5.00 μg/kg respectively.

The compounds of formula (I') wherein R' is as defined above also showed an intestinal prokinetic activity strictly related to their 5-HT$_3$ agonist action.

Said activity was investigated by means of a test aimed at evaluating fecal excretion in rats.

According to this test male rats weighing from 220 to 250 g were fasted for 3.5 hours in individual contention cages while water was provided ad libitum. The compounds of formula (I') to be tested were administered subcutaneously. The treatment schedule provided for 8 animals in each group.

At the time of drug treatment, the rectal lumen was manually emptied from any residual feces and the animals were then placed again into their cages.

90 Minutes after the treatment the fecal pellets were collected, their number was determined and their wet weight measured. They were then put in the oven and dried for 10 hours at 40° C. for the determination of the dry weight.

The parameter used to evaluate the activity of the test compounds was the dry weight (in grams) of the feces excreted during the 90 minutes following the subcutaneous administration of the test compound.

Almost no fecal excretion was observed in the concomitantly tested control animals which received the vehicle only.

In the animals treated with high doses, a maximum excretion of 12 to 16 fecal pellets with a dry weight of from about 1.4 to about 1.8 g, could be attained.

With total excretions exceeding the above values, diarrhoea is clearly observed and a correct quantification is impossible.

In this test the compounds of formula (I') showed a fairly good fecal excretion stimulating activity at very low doses.

As an example, in this test the 4-amino-1-(6-chloro-2-pyridyl)piperidine hydrochloride (the compound of formula (I') wherein R' is a chloro atom at position 6), at 2.5 mg/kg s.c. provoked the excretion of about 1.3 g of feces.

Said activity is related to the 5-HT$_3$ agonist activity as it is antagonised by selective 5-HT$_3$ receptor antagonists like zacopride and ICS 205-930.

On the basis of the found properties, the compounds of formula (I') are indicated for the treatment of those pathologies related to disorders of the serotoninergic systems, which are selectively mediated by the 5-HT$_3$ receptors.

The compounds of formula (I') wherein R' may represent hydrogen, a halogen atom, a methyl, methylthio, trifluoromethyl, trifluoromethylthio, $(C_1-C_3)$alkoxy, trifluoromethoxy, 2,2,2-trifluoroethoxy, or phenoxy group optionally substituted with a halogen atom, a trifluoromethyl, $(C_1-C_3)$alkyl, $(C_1-C_3)$alkoxy, $(C_1-C_3)$alkylthio, or cyano group, as well as their pharmaceutically acceptable salts, are therefore very interesting potential psychotropic agents, which may act through a mechanism involving 5-HT$_3$ receptors.

More particularly the above compounds, owing to their original mechanism of action, are mainly useful in the treatment of affective disorders and may also be useful in the treatment of some cases of anxiety or psychotic troubles. They may be useful also for the treatment of intestinal motility troubles and in particular of constipation.

In general, they may be employed in the treatment of all pathological disorders wherein a serotonin-like action selectively mediated by the 5-HT$_3$ receptors may be beneficial.

Furthermore, the compounds of formula (I') are poorly toxic, their toxicity being well compatible with a therapeutical utilisation.

The invention provides therefore for the use of the compounds of formula (I') wherein R' is as defined above for the preparation of medicaments suitable for the treatment or prophylaxis of the above indicated pathologies.

For the use in the treatment of the above pathologies, the compounds of formula (I') as well as their pharmaceutically acceptable salts, may conveniently be administered orally, parenterally, sublingually, rectally or transdermally, suitably formulated in pharmaceutical compositions.

The amount of active principle to be daily administered, will depend, as usual, on the particular therapeutical indication, on the severity of the disorders to be treated, as well as on the weight of the patient and the administration route.

In general, however, the daily overall dosage in humans varies between 0.05 and 100 mg, e.g. between 0.1 and 50 mg, and more conveniently between 0.5 and 20 mg.

The pharmaceutical compositions prepared by using the compounds of formula (I') and suited for the treatment of the above indicated pathologies, comprise at least one compound selected from the compounds of formula (I') and their pharmaceutically acceptable salts in admixture with a pharmaceutically inert vehicle.

They may be prepared according to conventional methods well known in the industrial pharmacy field.

The active principle may be admixed with the excipients conventionally employed in pharmaceutical compositions, such as talc, arabic gum, lactose, starch, magnesium stearate, aqueous or non-aqueous vehicles, animal or vegetable fats, paraffin derivatives, glycols, wetting, dispersing, emulsifying, preservative agents and the like agents.

For oral administration, which is, anyway, the most preferred route of administration, suitable pharmaceutical dosage forms comprise tablets, delayed release tablets, sugar coated tablets, capsules, suspensions, solutions, or also liposomes.

As for the intravenous, subcutaneous, or intramuscular administration, sterile or sterilisable solutions may be employed, while conventional suppositories, or rectal capsules or microoenemas can be used for rectal administration.

For transdermal administration, conventional patches prepared according to techniques well known to the persons skilled in the art can be employed.

Unit dosage forms for the new therapeutical use will typically comprise from 0.05 to 20 mg, preferably from 0.1 to 10 mg, including for instance from 0.5 to 5 mg (e.g. 0.5, 1, 1.5, 2, 2.5, 3, 3.5, 4, 4.5, and 5 mg) of active principle. These unit dosage forms are typically administered once or more times a day, preferably from 1 to 3 times a day.

If desired, the pharmaceutical compositions of the present invention may also contain one or more other active principles which are known and commonly employed for the same therapeutical indications.

We claim:

1. A method of inducing serotoninergic agonist action on 5-HT$_3$ receptors of a mammal which comprises administering to said mammal an effective amount of at least one compound of formula (I')

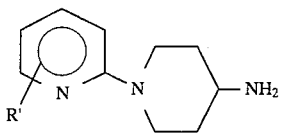

(I')

wherein R' represents hydrogen, a halogen atom, a methyl, methylthio, trifluoromethyl, trifluoromethylthio, ($C_1$–$C_3$)alkoxy, trifluoromethoxy, 2,2,2-trifluoroethoxy, or phenoxy group optionally substituted with a halogen atom, a trifluoromethyl, ($C_1$–$C_3$)alkyl, ($C_1$–$C_3$)alkoxy, ($C_1$–$C_3$)alkylthio, or cyano group, or of a pharmaceutically acceptable salt thereof.

2. The method of claim 1 wherein R' is at position 6- of the 2-pyridyl radical.

3. The method of claim 1 wherein R' represents a hydrogen atom or a halogen atom or a methyl or ($C_1$–$C_3$)alkoxy group at position 6-.

4. The method of claim 3 wherein the compound of formula (I') is selected from the group consisting of 4-amino-1-(6-chloro-2-pyridyl)piperidine, 4-amino-1-(6-bromo-2-pyridyl)piperidine, 4-amino-1-(6-methyl-2-pyridyl)piperidine, and 4-amino-1-(6-methoxy-2-pyridyl)piperidine and the pharmaceutically acceptable salts thereof.

5. The method of claim 4 wherein the compound of formula (I') is 4-amino-1-(6-chloro-2-pyridyl)piperidine or a pharmaceutically acceptable salt thereof.

6. The method of claim 1 wherein R' is a halogen atom at position 3-.

7. The method of claim 1 for the treatment of anxiety and psychotic troubles.

8. A method for the treatment of a mammal suffering from constipation which comprises administering to said mammal an effective amount of at least one compound of formula (I')

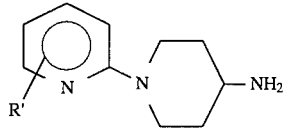

(I')

in which R' represents hydrogen, a halogen atom, a methyl, methylthio, trifluoromethyl, trifluoromethylthio, $C_1$–$C_3$ alkoxy, trifluoromethoxy, 2,2,2,-trifluorethoxy or phenoxy group optionally substituted with a halogen atom, a trifluoromethyl, $C_1$–$C_3$ alkyl, $C_1$–$C_3$ alkoxy, $C_1$–$C_3$ alkylthio or cyano group, or a pharmaceutically acceptable salt thereof.

* * * * *